United States Patent
Kousalik et al.

(10) Patent No.: US 9,347,889 B2
(45) Date of Patent: May 24, 2016

(54) CMOS OPTICAL DETECTOR WITH A PLURALITY OF OPTICAL ELEMENTS FOR DEVICE FOR MONITORING PARAMETERS OF A MOVING YARN ON TEXTILE MACHINES

(71) Applicant: Rieter CZ s.r.o., Usti nad Orlici (CZ)

(72) Inventors: Pavel Kousalik, Usti nad Orlici (CZ); Miroslav Stusak, Chocen (CZ); Ladislav Hajek, Brandys nad Orlici (CZ)

(73) Assignee: Rieter CZ s.r.o., Usti nad Orlici (CZ)

( * ) Notice: Subject to any disclaimer, the term of this patent is extended or adjusted under 35 U.S.C. 154(b) by 0 days.

(21) Appl. No.: 14/332,861

(22) Filed: Jul. 16, 2014

(65) Prior Publication Data
US 2015/0022813 A1  Jan. 22, 2015

(30) Foreign Application Priority Data

Jul. 16, 2013  (CZ) .................................. PV 2013-565

(51) Int. Cl.
*G01N 21/84* (2006.01)
*D01H 13/26* (2006.01)
*G01B 11/10* (2006.01)
(Continued)

(52) U.S. Cl.
CPC ............... *G01N 21/84* (2013.01); *D01H 13/26* (2013.01); *G01B 11/105* (2013.01); *G01B 11/2433* (2013.01); *G01N 21/8903* (2013.01); *G01N 21/8915* (2013.01); *G01N 33/365* (2013.01); *H01L 27/14643* (2013.01); *G01N 2021/8444* (2013.01); *G01N 2201/0438* (2013.01); *G01N 2201/061* (2013.01)

(58) Field of Classification Search
CPC .. D01H 13/26; G01B 11/105; G01B 11/2433; G01N 2021/8444; G01N 2021/8903; G01N 2021/8915; G01N 2201/0438; G01N 33/365; H01L 27/14643
USPC ...................... 356/237.1–241.6, 242.1–243.8, 356/426–431, 600–640
See application file for complete search history.

(56) References Cited

U.S. PATENT DOCUMENTS 2,991,685 A * 7/1961 Van Dongeren ............... 356/429
4,511,253 A * 4/1985 Glockner ............ G01B 11/105
250/559.24

(Continued)

FOREIGN PATENT DOCUMENTS

| GB | 2064106 A | * 10/1980 | ............ G01B 11/10 |
| GB | 2 064 106 | * 6/1981 | |
| WO | WO 99/36746 | 7/1999 | |

*Primary Examiner* — Tri Ton
*Assistant Examiner* — Jarreas C Underwood
(74) *Attorney, Agent, or Firm* — Dority & Manning, P.A.

(57) ABSTRACT

A CMOS optical detector includes a plurality of optical elements for a device for detecting parameters of moving yarn or another linear textile formation on textile machines by means of a perpendicular projection of yarn onto individual optical elements of a sensor with the aid of one source of radiation. The optical elements are arranged in two parallel rows perpendicular to the direction of the movement of the projection of yarn. Each optical element produces an output analog signal corresponding to the intensity of its irradiation. The individual optical elements of the first row are oriented to have their longer sides in the direction of the movement of the projection of yarn, whereas the optical elements of the second row are oriented to have their longer sides perpendicular to the direction of the movement of the projection of yarn.

11 Claims, 2 Drawing Sheets

(51) Int. Cl.
  *G01N 33/36* (2006.01)
  *G01N 21/89* (2006.01)
  *H01L 27/146* (2006.01)
  *G01B 11/24* (2006.01)

(56) References Cited

U.S. PATENT DOCUMENTS

| | | | | |
|---|---|---|---|---|
| 4,519,041 A | * | 5/1985 | Fant et al. | 382/141 |
| 4,895,449 A | * | 1/1990 | Marshall | G01B 11/046 250/559.15 |
| 4,948,260 A | * | 8/1990 | Felix | G01N 21/47 250/559.01 |
| 5,264,909 A | * | 11/1993 | Rochester | 356/73.1 |
| 5,383,017 A | * | 1/1995 | Schurch | G01N 33/365 356/238.3 |
| 5,592,849 A | * | 1/1997 | Nakade | B65H 63/06 57/265 |
| 5,694,495 A | * | 12/1997 | Hara et al. | 382/324 |
| 6,175,408 B1 | * | 1/2001 | Henze et al. | 356/238.3 |
| 6,219,135 B1 | * | 4/2001 | Hensel | G01B 11/105 250/559.45 |
| 6,242,755 B1 | * | 6/2001 | Henze | G01N 21/8915 250/221 |
| RE38,025 E | * | 3/2003 | Skunes et al. | 356/400 |
| 6,744,498 B2 | * | 6/2004 | Henze | D01H 13/26 250/559.4 |
| 7,057,197 B2 | | 6/2006 | Stusak | |
| 7,324,201 B2 | * | 1/2008 | Birlem | 356/429 |
| 8,509,487 B2 | * | 8/2013 | Lim | G01B 11/04 382/106 |
| 2004/0246473 A1 | * | 12/2004 | Hermary et al. | 356/237.1 |

* cited by examiner

CMOS OPTICAL DETECTOR WITH A PLURALITY OF OPTICAL ELEMENTS FOR DEVICE FOR MONITORING PARAMETERS OF A MOVING YARN ON TEXTILE MACHINES

TECHNICAL FIELD

The invention relates to a CMOS optical detector comprising a plurality of optical elements for monitoring parameters of moving yarn or another linear textile material on textile machines using perpendicular projection of yarn images on the optical elements of the detector by means of a single source of radiation.

BACKGROUND

CH 643 060 discloses a known device for determining the diameter of a linear body, such as yarn, in which the yarn to be measured moves across the area between a radiation source and an optical detector, in which the yarn diameter is determined by the width of the shadowed part of the detector, i.e. by the number of the shadowed radiation-sensitive elements. Nevertheless, this technical solution does not deal with the problem of the stability of the light source, nor does it allow a more detailed analysis of the surface structure of yarn.

The disadvantages of the solution according to CH 643 060 are eliminated by a method for detecting the thickness of a moving linear textile formation according to EP1051595B1 (CZ 286 113), in which the linear textile formation moves in a radiation flux between a radiation source and a CCD radiation sensor, which monitors the shadow of the moving linear textile material by evaluating the degree of irradiation of the individual elements of the CCD sensor. On the basis of the shadowed elements, the actual thickness of the linear textile formation is determined. The irradiation intensity of at least one irradiated element of the CCD sensor is continuously evaluated and the intensity of the radiation emitted by the radiation source depends on comparing the intensity of the irradiation of one chosen element of the CCD sensor with a predetermined value of irradiation, by which means the desired constant intensity of the irradiation of the elements of the CCD sensor is maintained during the operation.

A more accurate method for determination of the actual thickness of a moving linear formation according to this solution is achieved by monitoring and evaluating the intensity of irradiation of the elements of the CCD sensor on the delimitation lines of the image of the moving linear textile formation.

In order to determine the thickness and homogeneity of a moving linear textile formation according to this solution, the intensity of irradiation of the elements inside the delimitation lines of the image of the moving linear textile formation is monitored and evaluated.

The device for carrying out the method according to EP1051595B1 (CZ 286 113) was further improved, especially for the purpose of achieving better and more effective evaluation of a signal of a linear optical sensor and obtaining the most accurate data possible about the yarn diameter.

Obtaining the most accurate possible data on the yarn diameter is the object of other solutions, too. For example, the U.S. Pat. No. 6,242,755 B1 discloses a method for the contactless measuring of fibrous textile material of indeterminate length, in which the textile material is irradiated within a measuring range of at least one radiation source and its shadow is projected by the radiation onto the receiving device comprising a row of sensor cells arranged next to one another. The diameter of the fibrous textile material is determined on the basis of the shadowed sensor cells and one or two neighbouring sensor cells shadowed partially, whereby the value of the cells shadowed only partially by the image of the textile material is determined proportionally in a pro rata manner to the amount of fully shadowed images.

The drawback of this solution is the difficult and complicated evaluation of partially shadowed cells on the spinning machines operating online, which is caused by the oscillations or vibrations of the fibrous textile material in front of the row of sensor cells. An individual cell may also be shadowed partially as a result of the movement of yarn during the sensing (integrating) time interval and not as a result of an actual change in the yarn diameter.

It follows from what has been mentioned above that EP1051595B1 (CZ 286 113) and U.S. Pat. No. 6,242,755B1 provide a very similar method for determining the diameter of a linear textile formation, such as yarn. This is caused by the fact that EP1265051B1 has a priority date of Jan. 14, 1998 and was not published until Oct. 13, 1999 (as CZ 286 113) and Jul. 22, 1999 (EP1051595B1 as WO99/036746)), whereas the U.S. Pat. No. 6,242,755B1 has a priority date of Jul. 8, 1999, therefore patents EP1051595B1 (CZ 286 113) having an earlier priority date were published only after the priority date of U.S. Pat. No. 6,242,755B1 and do not constitute its background art.

The disadvantage of both solutions is the fact that only a minimal length of the overall length of the measured yarn is actually measured, whereby the values measured on very short sections of the length, for example when measuring yarn thickness, it is necessary to integrate in a complicated manner before the processing itself in order to eliminate or at least minimize the influence of accidental phenomena arising during measuring very short sections of yarn and at the same to achieve the required precision of measuring the yarn parameters. This is caused by the fact that the yarn moves in front of the sensor at a certain speed, e.g. at 1 m/s, whereby the common speed of monitoring yarn using CCD optical sensors is approximately 1×1 ms. Since the radiation-sensitive elements of the CCD optical sensors used for the contactless measuring of yarn have dimensions approximately 10 μm×10 μm, such a device can achieve at a speed of motion, such as 1 m/s, the actual measuring of yarn parameters only on 1% of its overall length, which has proved to be insufficient.

Therefore a device for the contactless measuring of yarn, capable of measuring a larger part of the overall length of yarn was developed and described in CZ 298929, whose principle consists in that the radiation-sensitive elements of the optical detector are rectangular-shaped and their dimensions in the direction of the movement of yarn are greater than their dimensions in a direction perpendicular to the direction of the movement of yarn, whereby the described dimension of the sensing elements in the direction of the movement of the yarn is in the range between 15 μm to 200 μm. This means that using the same speed of the movement of yarn and the same frequency of sensing, as is stated in the preceding paragraph, it is actually possible to measure the yarn parameters in the range from 1.5% to 20% of its overall length. The radiation sensor can be composed of a CMOS optical sensor or a CCD sensor. Each of the radiation-sensitive elements of the radiation sensor arranged in a row is coupled with an evaluation device of the state and/or intensity of their irradiation, whereby the evaluation device can be an integrated part of the radiation sensor. The disadvantage of this device is especially meeting high demands for data transmission between the sensor and the processor, which results in higher requirements on the connected processor and, on the whole, it decreases the evaluation potential of the device.

The shortcomings of CZ 298929 were eliminated by a device for the contactless measuring of the properties of moving yarn according to CZ 299684, in which a linear optical sensor is incorporated on one semiconductor application specific integrated circuit (ASIC) together with at least a part of electronic circuits for processing and/or evaluation of a signal of the linear optical sensor, whereby the electronic circuits for processing and/or evaluation of a signal of the linear optical sensor are arranged along with the linear optical sensor on a common semiconductor support and/or arranged in one common case.

The advantage of such an arrangement is especially the fact that the initial operations of processing and/or evaluation of a signal of the sensor take place in one integrated circuit, and so they are not limited by the possibilities of the data flow between the sensor and the processor, since from the outlet of the device it is not necessary to transmit detailed information about which pixel is irradiated and which is not, but the data on the yarn diameter is transmitted directly in the digital form, whereby the data on the yarn diameter has substantially lower demands for data transmission, because for 1000 pixels, for example, it is not necessary to transmit 1000 bits of information, but only 10 bits of information about the width of yarn, or about the number of continuously shadowed and/or irradiated pixels. The circuits for processing and/or evaluation of a signal integrated with the sensor are able to use the same frequency as the sensor, which nowadays usually amounts to 20-40 MHz in the case of CMOS linear optical sensors.

The drawback of this solution is a purely digital evaluation system of individual pixels, when, according to the set comparison level, pixels are divided into irradiated and non-irradiated, the yarn diameter being determined by the sum of the width of the radiated pixels. In addition, it is difficult to monitor possible dusting on the pixels or on the radiation source, as well as their aging process.

EP 1015873 B1 describes a device for recording at least one parameter of a linear body which moves longitudinally, through an optical detector which is made up of two separate sensors, at least one of them being digital and at least one being analog. The detector thus comprises two types of sensors that work according to different principles or whose signals are evaluated according to different principles, one of the principles being digital and the other analog.

The advantages of this solution consist especially in the fact that apart from the diameter of a relatively smooth body, also the surface structure of the monitored body can be measured within certain limits. In the case of yarn it is, for example, possible to measure digitally the body of yarn without protruding fibers, and in the analog manner the hairiness of yarn, i.e. the percentage of fiber ends sticking out of the yarn. With the aid of the evaluation technology, this detector can be even adapted to the changed conditions of measuring and compensate for or take into account, for example, the influence of impurities and residues on the sensors. The optical detector, however, cannot be adapted to changes in external radiation and/or aging of the light source.

The disadvantage of this solution is particularly the fact that two types of different sensors are used, i.e. digital and analog, whereby signals from both types of sensors are received and recorded completely separately, and in this form they are transmitted to a superior evaluation device to be processed, which, especially in the case of the analog channel, results in the necessity of subsequent digitalization of the data obtained in this manner and their primary processing as late as in the evaluation device. This places unacceptably high demands on the computing capacity of the evaluation device, especially during on-line processing of the data on spun-out yarn which takes place directly on the production machine. Furthermore, the necessity of the correlation of the signals from the digital and analog sections of the sensor is also demanding as to the computing capacity, if it is carried out by purely programming means, as is described in the patent application. Moreover, uncontrollable movements of the yarn in a direction perpendicular to its basic production movement may unfavourably influence the analog signal obtained from the analog sensor or sensors. Apparently, this arrangement is acceptable when used in a laboratory measuring device, where the quality of yarn is evaluated off-line at a suitable speed and with proper stabilization of the position of yarn in front of a sensor, but using sensors online directly on spinning or weft-winding machines is thoroughly unsuitable both from the technical and from the economic point of view.

Another disadvantage of this device following from entirely independent processing of the signals from the digital and analog sections is the fact that each of these channels exhibits different types of errors which are dependent, for example, on the temperature or ambient light and, in the case of an analog channel, they are dependent also on noise and electromagnetic disturbing signals induced into the analog conductor which on the basis of the principle described in the patent must have a certain minimal length within which it is exposed to the influence of electromagnetic disturbance from the surrounding devices of the spinning machine.

Disturbance-free environment can be evidently created in the case of a measuring device used in a laboratory, but not when used on-line on a spinning or weft-winding machine.

Apart from the above-mentioned method for detecting thickness by a linear CCD sensor, EP1051595B1 (CZ 286 113) also describes a method for continuous monitoring of a moving linear textile formation, in which the moving linear textile formation is monitored in a plurality of planes of sensing, since the linear textile formation moves between a flat radiation source and a matrix CCD sensor, and so it should be able to be used on-line on a textile machine. The evaluation of the state and/or intensity of irradiation, however is carried out in each of the elements of the matrix CCD sensor in individual lines. The evaluation is therefore complicated, slow, and expensive, and so the device cannot be used on textile machines producing or processing yarn, such as spinning or weft-winding machines.

SUMMARY OF THE INVENTION

An aim of the invention is to provide an optical detector for a device for detecting the parameters of moving yarn, which can be used directly on spinning or weft-winding machines and which, compared to the background art, serves to obtain information about yarn defects of greater length expansion, especially defects having a slowly changing diameter. Also, the device ensures higher accuracy and sensitivity of measuring and at the same time has high resistance to external influences, such as ambient light or aging of the light source. Another objective is to carry out a large part of mathematical operations connected to the monitoring of the parameters of yarn directly in the optical detector. During spinning, especially during spinning from raw materials of lower quality, dust coating covers the detection zone of the detector and/or the outlet zone of the light, which may very negatively influence the results of measuring. Therefore, another goal of the invention is to reduce the optical detector fouling to the maximum extent possible.

Additional objects and advantages of the invention will be set forth in part in the following description, or may be obvious from the description, or may be learned through practice of the invention.

The aim of the invention is achieved by an optical detector comprising a plurality of optical elements arranged in two parallel rows perpendicular to the direction of the movement of the projection of yarn, whereby each optical element produces at its output an analog signal corresponding to the intensity of its irradiation and each optical element is rectangular-shaped. The optical elements of the first row are oriented to have their longer sides in the direction of the movement of the projected image of yarn, whereas the optical elements of the second row are oriented to have their longer sides perpendicular to the direction of the movement of the projected image of yarn.

The sensor of the optical detector is constructed in such a manner that it can provide complex information about the properties of spun-out yarn and at the same time enable to eliminate negative influences of the environment. This is achieved by using two rows of optical elements, whereby the individual optical elements provide at their outputs analog signals, corresponding to the intensity of irradiation, wherein these rows consist of rectangular optical elements which are oriented in each row mutually perpendicular. The first row of optical elements primarily serves to detect the yarn diameter and the current position of yarn in front of the sensor for the purpose of masking the optical elements of the second row. The second row of optical elements serves above all to obtain information about external lightning, the degree of dusting of the sensor, and about the surface structure.

From the point of view of geometry and quality of monitoring spun-out yarn, it is advantageous if the ratio of shorter and longer sides of the optical elements in the first row ranges from 1:10 to 1:200, preferably 1:100. Due to this ratio of the side lengths, and due to the existing potential of the current semiconductor technology, the length of the longer side of a rectangular pixel of the first row is found to be in the range between 0.05 and 0.4 mm. Thus, on this length, the signal about the yarn diameter is integrated directly on the sensor also in an analog manner, and so it is ensured that all the sections of yarn will be measured, but at the same time this length is smaller than the smallest defects that are being monitored in the yarn. Neps are typically longer than 1 mm, whereas defects with a slowly changing diameter are a manifold longer. Therefore, it appears optimal to use an optical element having such a length that the length of the yarn passing in front of the optical element during one sensing would be the same as the length of the optical element at an assumed maximum speed of the measured linear textile formation.

The ratio of shorter sides to longer sides of the individual optical elements in the second row is in the range between 1:2 and 1:10, preferably 1:5. The reason for this choice is in particular the comparability of the length of the longer side of an optical element of the second row having a diameter of usually spun-out yarn, which during the processing of the signals from the optical elements of the second row enables— by suitable masking the completely irradiated optical elements and/or completely shadowed optical elements—to increase the precision of the evaluation of the surface structure of yarn. On the other hand, a very short length is selected for the shorter side of an optical element of the second row, namely for the purpose of obtaining as many details as possible about the surface structure of the yarn.

It is also advantageous if the ratio of the number of the individual optical elements of the second row to the number of individual optical elements of the first row is in the range between 10:100 and 20:2000, preferably 16:1024. This arrangement guarantees obtaining relevant data both on the yarn diameter, as a result of the integration of the signal on the first row of optical elements, and on the surface structure as a result of using the optical elements of the second row, which are only partially irradiated, on the basis of the data on the position of yarn in front of the detector which was obtained from the first row of optical elements.

In order to increase the precision of measuring and ensure that substantially identical section of yarn is always measured by both rows, the distance between both rows of optical elements is smaller than the length of the longer side of the rectangular-shaped optical element of the first row and, at the same time, the distance between the outer side of the optical elements of the first row and the outer side of the optical elements of the second row is at the most twice as long as the longer side of the optical elements of the first row.

Owing to the fact that each optical element of the sensor produces at its output an analog signal, any fully irradiated optical element of the first row and/or of the second row can be used to obtain information about external light, a degree of dust cover of the sensor, or about the aging of the radiation source. Since the sensor is capable of distinguishing between fully irradiated, partially irradiated and fully shadowed optical elements, this information can be obtained from the sensor also when the yarn is moving in the sensor. By comparing the values of fully irradiated optical elements and/or their changes, it is possible to identify and, possibly, also compensate for different external influences.

The outlets of the individual optical elements of the first row are connected to at least one analog-to-digital converter through one or several analog multiplexers, whereby the outlet of each optical element of the second row is connected to an inlet of an analog-to-digital converter. Due to a great number of optical elements of the first row, using multiplexers leads to reducing the number of analog-to-digital converters needed, and that results in decreasing the surface area of the semiconductor support on which they are arranged and, consequently, the price of the optical detector is lower.

The analog-to-digital converter/converters for groups of optical elements of the first row has/have a lower resolution than the analog-to-digital converters for the individual elements of the second row. Owing to the fact that the first row of optical elements serves primarily to measure the yarn diameter, and in the distance corresponding to the longer side of the rectangular optical element, a signal is integrated from the length of yarn which corresponds to this distance, a lower resolution of the analog-to-digital converter is sufficient to fulfill its function adequately. Due to the properties of the semiconductor structure, this analog-to-digital converter exhibits lower digitized noise levels. Also, this solution is justified by the impact on the required surface area of the semiconductor support of the optical detector in order to realize an analog-to-digital converter with a higher resolution.

The optical elements in both parallel rows are arranged on a common semiconductor support along with the analog multiplexers of the first row and the corresponding analog-to-digital converters for processing the analog output signals of the optical elements, whereby the outlets of all the analog-to-digital converters are connected to the inlet of a programmable device of the optical detector, such as a microprocessor or a field programmable device (FPGA, CPLD), which is arranged on the same semiconductor support. Integrated pre-processing of analog signals by a programmable device directly in the optical detector enables to eliminate disturbing signals, which always burden transmissions of analog signals over longer distances, and also makes it possible to reduce considerably the computing power of the connected processor in the yarn cleaner during the subsequent processing of the data and evaluation of yarn defects. All the necessary data needed for the actual process of evaluation of the yarn quality in the yarn cleaner is obtained from the optical detector already preprocessed and prepared. Thus the optical detector itself continuously samples the yarn on its maximum frequency in order to prevent loss of information at high speeds of the movement of yarn, passing the already preprocessed relevant information to the programmable device of the yarn cleaner and/or a superior system.

In addition, the programmable device of the optical detector advantageously comprises digital programmable means for the complex processing of the data from the outputs of the analog-to-digital converters, corresponding to the optical elements of both rows. By means of the digital programmable means, it is possible to preprocess the data more simply and even extremely efficient algorithms can be applied. Programming enables to control and change the method for preprocessing data for various applications and/or for meeting various requirements of the programmable device of the yarn cleaner and/or of the superior system during the operation of the machine. Moreover, a possible change of an integrated programme is considerably simpler than a completely new proposal of a new semiconductor structure of the optical detector.

It is advantageous for the communication with the superior system and/or the programmable device of the yarn cleaner if, on the common semiconductor support, there are integrated circuits for the communication with these devices.

In another embodiment on a common semiconductor support, preferably in the programmable device of the image sensor, there are integrated also digital programmable means for the evaluation of the quality of yarn and for the classification of yarn defects and there is no need to use a programmable device of the yarn cleaner or a programmable device with a considerably lower performance can be used.

The two rows of rectangular optical elements are located on a common semiconductor support spaced closely to one another, thus providing at any instant information about virtually identical section of yarn. This can be stated with a high degree of precision with respect to the common source of radiation, arrangement of the optical system and specific dispersion of radiation in the direction of the movement of yarn. Also, located on a common semiconductor support are all the necessary electronic evaluation circuits which process analog output signals from both rows of the optical elements.

A main benefit of the solution according to the invention is that all the signals providing complete information about the yarn parameters obtained from both rows of the optical elements are either processed directly in the optical detector so that at the outlet of the optical detector complex information about the instantaneous parameters of the monitored section of yarn is generated, and this complex information is transmitted to the programmable device of the yarn cleaner for the evaluation of the quality of the spun-out or processed yarn and detecting defects in it. Thus the computing power of this programmable device of the yarn cleaner is not encumbered with the real-time processing of huge amounts of data and can be used for the sophisticated evaluation of the instantaneous quality of yarn, detection and classification of defects, all that being achieved with low costs, which is essential if we take into account the fact that these yarn cleaners are applied directly on production machines comprising a plurality of operating units.

DESCRIPTION OF DRAWINGS

An example of embodiment of the detector according to the invention is schematically shown in the enclosed drawings, where.

DETAILED DESCRIPTION OF PARTICULAR EMBODIMENTS

Reference will now be made to embodiments of the invention, one or more examples of which are shown in the drawings. Each embodiment is provided by way of explanation of the invention, and not as a limitation of the invention. For example features illustrated or described as part of one embodiment can be combined with another embodiment to yield still another embodiment. It is intended that the present invention include these and other modifications and variations to the embodiments described herein.

The device for detecting the parameters of moving yarn on textile machines, such as spinning machines or weft-winding machines, comprises a case 1, in which there is formed a groove 11 for the passage of yarn 2. The groove 11 is open on one side, which enables to insert the yarn 2 into the groove 11. Arranged opposite each other in the side walls of the groove 11 are an outlet portion of a source 3 of radiation and a sensor 4 of an optical detector 5.

In the illustrated embodiment, the source 3 of radiation comprises a light-emitting diode 31 and an optical lens 32 that serves to create a bundle of parallel rays passing through the groove 11 and projecting a shadow on the sensor 4 of the optical detector 5 as a result of the perpendicular projection of the yarn 2 projection.

Figure 3:
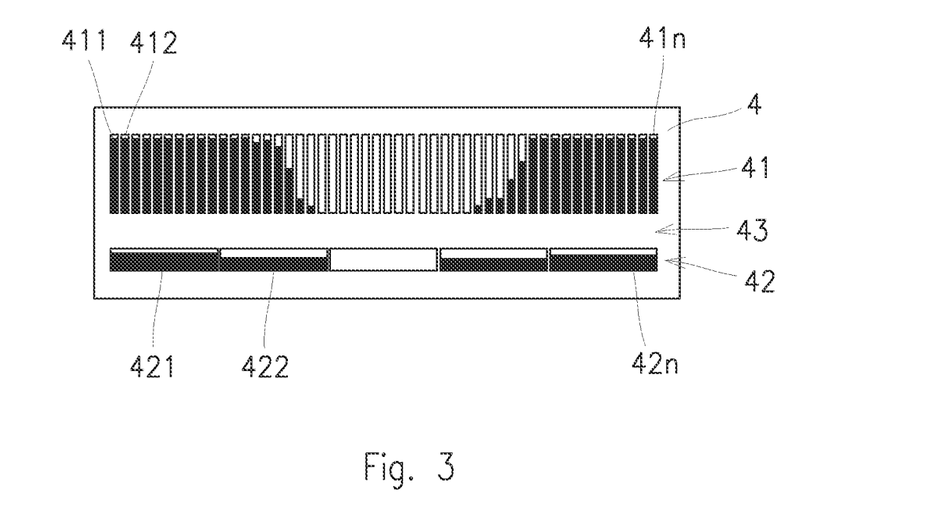
FIG. 3 shows a sensor.

The sensor 4 of the optical detector 5 comprises two parallel rows of optical elements. The optical elements 41 of the first row are rectangular-shaped and are oriented to have their longer sides in a direction of the movement of the yarn 2 projection. The optical elements 42 of the second row are also rectangular-shaped, but they are oriented to have their longer sides perpendicular to a direction of the movement of the yarn 2 projection. At the output of the optical elements 41 of the first row, as well as at the output of the optical elements 42 of the second row, there is an analog signal which is proportionate to the intensity of irradiation or shadowing of the corresponding optical element 41, 42. The optical elements 41, 42 of both rows are created by CMOS technology. FIG. 3 schematically represents the optical elements 41, 42 of the sensor 4, on which the image of the yarn 2 is projected, whereby the black colour in individual optical elements 41, 42 indicates the size of the analog signal emitted by the completely or partially irradiated optical elements 41, 42.

In the illustrated and described example, the dimensions of each individual optical element 411, 412, ... 41n of the first row are 2×200 µm, their spacing being 4 µm, which means that the distance between the individual optical elements is 2 µm. A usual number of the individual optical elements 411, 412, ... 41n of the first row is 1024. From this, it follows that the length of the first row of the optical elements is approximately 4 mm, whereby the diameters of the monitored yarn formations are in the order of tens to hundreds of µm and the diameters of the yarn defects may be several times larger than the yarn diameter. It follows from the above-mentioned facts that in the illustrated example, the ratio of the shorter and longer sides of the optical elements 41 of the first row is 1:100.

The light sensitivity of the optical element is defined by its surface area. If the surface area of the optical element is small, its sensitivity is also small and it is necessary to use a greater light performance of the radiation source. Owing to the fact that the optical elements for monitoring the width of the yarn projection are required to be as narrow as possible, since the width of the optical element and spacing between the optical elements determines the precision of measuring, and therefore a certain length of the optical element is needed, combined with the potential of the radiation source, in order to achieve optimal sensitivity. If we define an optical element by the ratio of its shorter and longer sides, it is the ratio 1:10 that appears to be the lower limiting value and the ratio to 1:200 appears to be the upper limiting value. These values can be used while still maintaining acceptable economic conditions.

The optical detector 5 usually works on its maximum frequency, such as 40,000 samples per second. Therefore it appears ideal to use an optical element having such a length that the length of yarn passing in front of the optical element during sensing would be the same as the length of the optical element at an assumed speed of yarn. If an assumed speed of yarn is 480 m/min, it corresponds to the speed of 8 m/s, i.e. 8,000 mm/s. Thus 8,000 mm of the monitored yarn 2 moves in front of the detector 5 in one second, which means that during each sampling there is 0.2 mm (200 µm) of the length of yarn 2 in front of the sensor.

In the illustrated and described embodiment, the dimensions of each optical element 42 of the second row are 254×50 µm, their spacing being 256 µm, which means that the distance between the optical elements 42 of the second row is 2 µm. The usual number of the optical elements 42 of the second row is 16, and so the length of the second row of optical elements is the same as the length of the first row of optical elements, i.e. approximately 4 mm. From this, it follows that in the illustrated embodiment, the ratio of the shorter and longer sides of the optical elements 42 of the second row is approximately 1:5. It is apparent to those skilled in the art that also the ratio of shorter and longer sides of the individual optical elements 42 of the second row can be to a certain extent modified without negative influences on the precision of measuring this row and the system of both rows of optical elements. The optimal ratio appears to be in the range between 1:2 to 1:10.

Both rows of individual optical elements 41, 42 are located closely spaced to one another so that they could provide information about a substantially identical section of yarn 2 at any instant. The distance 43 between the first row of optical elements 41 and the second row optical elements 42 is shorter than the length of the longer side of the rectangular-shaped optical element 41 of the first row and at the same time the distance between the outer side of the optical elements 41 of the first row and the outer side of the optical elements 42 of the second row is at the most twice as long as is the longer side of the optical elements 41 of the first row. If the second row of optical elements 42 is located close to the first row of optical elements 41, both rows of optical elements provide information about a substantially identical section of yarn 2.

The outputs of the optical elements 41, 42 are processed in an analog manner and subsequently by analog-to-digital converters so that the precise value of intensity of irradiation of the optical elements 41, 42 of each row is obtained, as is shown in FIG. 3.

Figure 1:
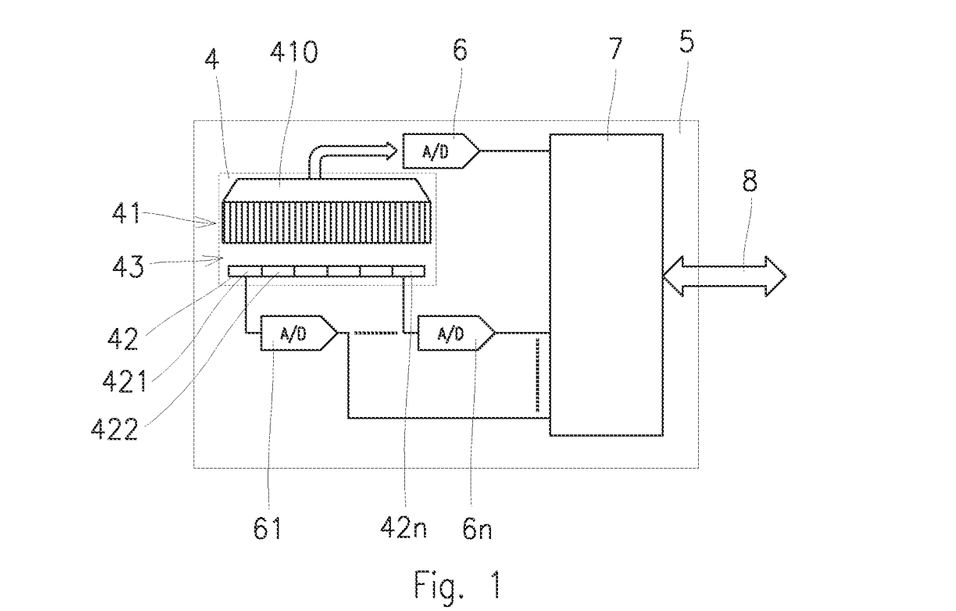
FIG. 1 shows an arrangement of the detector.

An example of connection of the optical detector 5 is schematically represented in FIG. 1, where the dashed line indicates a semiconductor support, arranged on which is the first row of optical elements 41 of the sensor 4. The outlets of the individual optical elements 411, 412, ... 41n of the first row are connected by means of one or several analog multiplexers 410 to one or several analog-to-digital converters 6, whereby in the illustrated embodiment one multiplexer 410 and one analog-to-digital converter 6 are used. The analog multiplexers 410 and analog-to-digital converter/converters 6 are arranged on a common semiconductor support along with the optical elements 41 of the first row of the sensor 4.

Ideally, each individual optical element should have its own fast analog-to-digital converter with a high resolution. The higher the resolution of the converter, the larger the required chip area and, naturally, the higher the price of the device. Therefore it is favourable to use analog multiplexers and a smaller number of analog-to-digital converters for the first row containing a plurality of optical elements. Arranged on this common semiconductor support is also the second row of optical elements 42 of the sensor 4. The second row is parallel with the first row and the outlet of each individual optical element 421, 422, ... 42n of the second row is connected to the inlet of the analog-to-digital converter 61, 62, ... 6n, these analog-to-digital converters being arranged on a common semiconductor support with the above-described elements. Analog-to-digital converters 61, 62, ... 6n limit by their number and required area the number of individual optical elements 421, 422, ... 42n of the second row. Therefore also for the second row, analog multiplexers can be used, as well as a smaller number of analog-to-digital converters, as is shown and described in the case of the first row. The outlets of all the analog-to-digital converters 6, 61, 62, ... 6n are connected to the inlet of the programmable device 7 of the optical detector (microprocessor, FPGA/CPLD), which is arranged on a common semiconductor support and which comprises digital means of processing the information from both rows of the individual optical elements 41, 42 of the sensor. The programmable device 7 of the detector 5 comprises unillustrated digital means and/or digital programmable means for complex processing of the data from the outlets of the analog-to-digital converters 6, 61, 62, ... 6n corresponding to the optical elements 41, 42 of both rows.

The programmable device 7 of the optical detector 5 makes it possible to preprocess the data obtained from the individual optical elements 41, 42 in a simpler manner and to apply highly efficient algorithms. Moreover, a possible modification of the integrated program is substantially simpler than a completely new proposal of the surface structure of the optical detector 5.

Programming enables to control and modify the method for preprocessing data for various applications and/or for various requirements from the superior system during the operation.

The means of the programmable device 7 of the optical detector 5 serve to preprocess the data directly in the detector, by which means the load during the subsequent processing operations is significantly lowered. The optical detector 5 provides all the necessary data already preprocessed and prepared for the actual evaluation of the quality of yarn 2. The optical detector 5 itself in this manner continuously samples the yarn 2 on its maximum frequency so as to eliminate loss of information at high speeds of the movement of yarn 2. The initial data thus sampled does not have to be transmitted between the optical detector 5 and other units for processing, for example by means of communication data buses, but is preprocessed directly in the detector 5 at a high speed. For further processing, the optical detector 5 provides data that facilitates further evaluation.

Figure 2:
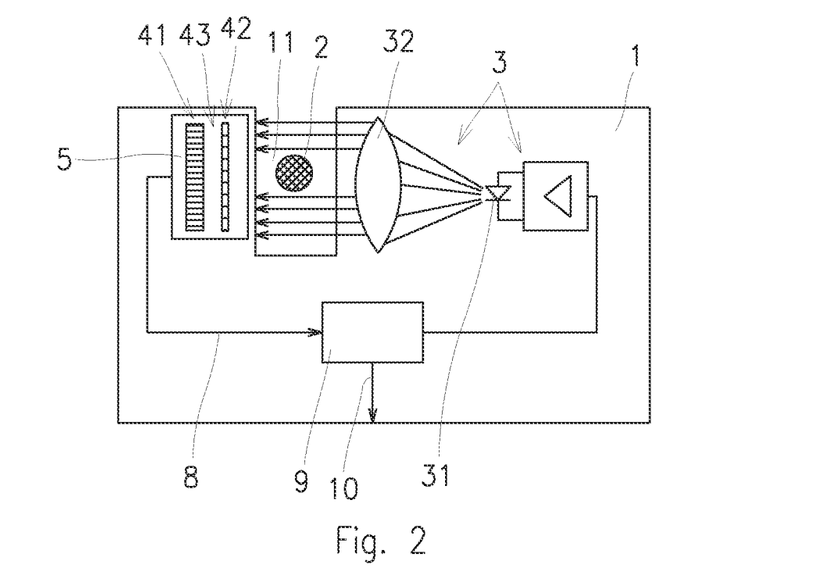
FIG. 2 illustrates an arrangement of the yarn cleaner.

In the illustrated embodiment, on a common semiconductor support of the optical detector 5, there are integrated circuits of a communication data bus 8 for the communication with a programmable device 9 of a yarn cleaner for the evaluation of the quality of yarn 2 and classification of yarn 2 defects. The programmable device 9 of the yarn cleaner is coupled with a communication data bus 10 of the yarn cleaner for the data transmission from the yarn cleaner to the superior systems and for controlling the yarn cleaner by these superior systems.

In an unillustrated embodiment, the digital programmable means for evaluation of the quality of yarn 2 and classification of yarn 2 defects are part of the programmable device 7 of the optical detector 5.

The analog-to-digital converter/converters 6 for groups of optical elements 41 of the first row have a lower resolution than the analog-to-digital converters 61, 62, . . . 6n for the individual optical elements 421, 422, . . . 42n of the second row.

The optical detector according to the invention can be used on machines for production and/or processing yarn and yarn-like linear textile formations.

Modifications and variations can be made to the embodiments illustrated or described herein without departing from the scope and spirit of the invention as set forth in the appended claims.

The invention claimed is:

1. A CMOS optical detector for detecting parameters of a moving linear textile formation, such as a yarn, in textile machines, the detector comprising:
   a sensor having a plurality of the optical elements, wherein an image of the textile formation is projected onto the optical elements with a single radiation source, the optical elements configured in first and second parallel rows that extend perpendicular to a direction of movement of the image, the first and second parallel rows of optical elements provided as separate and spaced apart arrays;
   each optical element having an overall rectangular shape and produces an output analog signal that is proportional to irradiation intensity on the optical element from the radiation source;
   the optical elements of the first parallel row are oriented to have their longer sides in the direction of movement of the image; and
   the optical elements of the second parallel row are oriented to have their longer sides perpendicular to the direction of movement of the image.

2. The optical detector as in claim 1, wherein a ratio of shorter to longer side of the optical elements of the first parallel row is from 1:10 to 1:100.

3. The optical detector as in claim 2, wherein a ratio of shorter to longer side of the optical elements of the second parallel row is from 1:2 to 1:10.

4. The optical detector as in claim 3, wherein a ratio of the number of the optical elements in the second parallel row to the number of the optical elements in the first parallel row is from 10:100 to 20:2000.

5. The optical detector as in claim 1, wherein a distance between the first and second parallel rows of optical elements is less than a length of longer sides of the optical elements in the first parallel row of optical elements, and a distance between an outer side of the optical elements in the first parallel row and an outer side of the optical elements in the second parallel row is not more than twice as long as the length of longer sides of the optical elements in the first parallel row.

6. The optical detector as in claim 1, wherein the respective output analog signals from the optical elements in the first parallel row are connected to one or more analog-to-digital converters through one or more multiplexers, and the output analog signal from each of the optical elements in the second parallel row are connected to individual respective analog-to digital converts directly or through an multiplexer.

7. A CMOS optical detector for detecting parameters of a moving linear textile formation, such as a yarn, in textile machines, the detector comprising:
   a sensor having a plurality of the optical elements, wherein an image of the textile formation is projected onto the optical elements with a single radiation source, the optical elements configured in first and second parallel rows that extend perpendicular to a direction of movement of the image;
   each optical element having an overall rectangular shape and produces an output analog signal that is proportional to irradiation intensity on the optical element from the radiation source;
   the optical elements of the first parallel row are oriented to have their longer sides in the direction of movement of the image;
   the optical elements of the second parallel row are oriented to have their longer sides perpendicular to the direction of movement of the image;
   wherein the respective output analog signals from the optical elements in the first parallel row are connected to one or more analog-to-digital converters through one or more multiplexers, and the output analog signal from each of the optical elements in the second parallel row are connected to individual respective analog-to digital converts directly or through an multiplexer, and
   wherein the analog-to-digital converters associated with the optical elements in the first parallel row have a lower resolution than the analog-to-digital converters associated with the optical elements in the second parallel row.

8. A CMOS optical detector for detecting parameters of a moving linear textile formation, such as a yarn, in textile machines, the detector comprising:
   a sensor having a plurality of the optical elements, wherein an image of the textile formation is projected onto the optical elements with a single radiation source, the optical elements configured in first and second parallel rows that extend perpendicular to a direction of movement of the image;
   each optical element having an overall rectangular shape and produces an output analog signal that is proportional to irradiation intensity on the optical element from the radiation source;
   the optical elements of the first parallel row are oriented to have their longer sides in the direction of movement of the image;
   the optical elements of the second parallel row are oriented to have their longer sides perpendicular to the direction of movement of the image;
   wherein the respective output analog signals from the optical elements in the first parallel row are connected to one or more analog-to-digital converters through one or more multiplexers, and the output analog signal from each of the optical elements in the second parallel row are connected to individual respective analog-to digital converts directly or through an multiplexer, and
   wherein the first and second parallel rows of optical elements, the analog-to-digital converters associated with the optical elements in the first parallel row, and the analog-to-digital converters associated with the optical elements in the second parallel row are arranged on a common semiconductor support, and further comprising a programmable device in connected to the analogto-digital converters associated with the first and second parallel rows of optical elements also arranged on the common semiconductor support.

9. The optical detector as in claim 8, wherein the programmable device is configured to digitally process output signals from the analog-to-digital converters associated with the first and second parallel rows of optical elements.

10. The optical detector as in claim 9, further comprising circuits arranged on the common semiconductor support for communication with a yarn cleaner programmable device.

11. The optical detector as in claim 9, wherein the programmable device evaluates the output signals from the analog-to-digital converters for yarn quality parameters and classification of yarn defects.

* * * * *